United States Patent
Watanabe et al.

(10) Patent No.: US 10,236,083 B2
(45) Date of Patent: Mar. 19, 2019

(54) VISUALIZATION APPARATUS AND VISUALIZATION METHOD

(71) Applicants: FUJITSU LIMITED, Kawasaki-shi, Kanagawa (JP); The University of Tokyo, Tokyo (JP)

(72) Inventors: Masahiro Watanabe, Kawasaki (JP); Yoshimasa Kadooka, Kawasaki (JP); Toshiaki Hisada, Tokyo (JP); Seiryo Sugiura, Tokyo (JP); Takumi Washio, Tokyo (JP); Jun-Ichi Okada, Tokyo (JP)

(73) Assignees: FUJITSU LIMITED, Kawasaki (JP); THE UNIVERSITY OF TOKYO, Tokyo (JP)

( * ) Notice: Subject to any disclaimer, the term of this patent is extended or adjusted under 35 U.S.C. 154(b) by 366 days.

(21) Appl. No.: 14/794,039

(22) Filed: Jul. 8, 2015

(65) Prior Publication Data
US 2016/0019363 A1 Jan. 21, 2016

(30) Foreign Application Priority Data
Jul. 17, 2014 (JP) .................................. 2014-146637

(51) Int. Cl.
*G16H 50/50* (2018.01)
*G06F 19/00* (2018.01)

(52) U.S. Cl.
CPC ............. *G16H 50/50* (2018.01); *G06F 19/00* (2013.01)

(58) Field of Classification Search
CPC .......................... G06F 19/3437; A61B 34/25
USPC ........................................................... 703/9
See application file for complete search history.

(56) References Cited

U.S. PATENT DOCUMENTS

| | | | |
|---|---|---|---|
| 2011/0235883 A1 | 9/2011 | Nakagawa et al. | |
| 2012/0041318 A1 | 2/2012 | Taylor | |
| 2012/0041739 A1* | 2/2012 | Taylor | A61B 5/02007 703/11 |
| 2013/0304445 A1 | 11/2013 | Iwamura et al. | |

FOREIGN PATENT DOCUMENTS

| | | |
|---|---|---|
| JP | 2004-201730 | 7/2004 |
| JP | 2011-200549 | 10/2011 |
| JP | 2013-534154 | 9/2013 |

(Continued)

OTHER PUBLICATIONS

Circumference_Defined_2013 (archived definition dated Jun. 23, 2013 downloaded from https://en.wikipedia.org/w/index.php?title=Circumference&oldid=561136789).*

(Continued)

*Primary Examiner* — Brian S Cook
(74) *Attorney, Agent, or Firm* — Staas & Halsey LLP

(57) ABSTRACT

A visualization apparatus includes a memory unit and a computing unit. The memory unit stores a circulation model in which a vascular network, of an organ, having a diameter equal to or smaller than a predetermined value is defined on a two-dimensional plane, and a simulation result of a blood flow in the vascular network of the circulation model. The computing unit transforms the circulation model into a three-dimensional structure including the vascular network located on a cylindrical surface of a cylinder, and displays the simulation result on the three-dimensional structure.

4 Claims, 18 Drawing Sheets

(56) References Cited

FOREIGN PATENT DOCUMENTS

| JP | 2013-233369 | 11/2013 |
|---|---|---|
| WO | WO 2012/021307 A2 | 2/2012 |

OTHER PUBLICATIONS

Small_Intestine_2014 (Archived definition dated Jan. 27, 2014 downloaded from https://en.wikipedia.org/w/index.php?title=Small_intestine&oldid=592690379).*

Kretowski_2007 (Simulation of bipasic CT findings in hepatic cellular carcinoma by a two-level physiological model, IEEE Trans Biomed Eng., 2007; 54(3): 538-542).*

Villi_2011 (Villi in the small intestine, University of Waikato, 2011).*

Goldman_2000 (A computational Study of the Effects of Capillary Network Anastomoses and Tortuosity on Oxygen Transport, J. Theo. Biol. (2000) 206, 181-194).*

Bullitt_2003 (Measuring Tortuosity of the Intracerebral Vasculature from MRA Images IEEE Trans Med Imaging. Sep. 2003; 22 (9): 1163-1171.).*

Goldman_2008 (Theoretical Models of Microvascular Oxygen Transport to Tissue, Microcirculation. Nov. 2008; 15(8): 795-811. Doi:10/1080/10739680801938289).*

Brunnett_2004 (Geometric Modeling for Scientific Visualization, Mathematics and Visualization Series, Springer-Verlag 2004).*

Poole, J.B., 2013 The Office Drawing Tools, Essential Microsoft Office 2013: Tutorials for Teachers.*

Alspaugh, J.C., 1992 A Short Guide to AutoCAD Drawing Primitives for 3D Computer Graphics Models and the Walkthrough AutoCAD-to-Polygon Conversion Proram.*

Create Basic 3D Objects dated 2009 downloaded from http://gtu.ge/Arch/Faculty/Multimedia/Acad_11/11create_basic_3dobjects0/create_basic_3Dobjects.pdf.*

Patent Abstracts of Japan, Publication No. 2011-200549, published Oct. 13, 2011.

Patent Abstracts of Japan, Publication No. 2004-201730, published Jul. 22, 2004.

Espacenet Bibliographic data, Publication No. 2013-534154, published Sep. 2, 2013.

Patent Abstracts of Japan, Publication No. 2013-233369, published Nov. 21, 2013.

Kassab et al., "A hemodynamic analysis of coronary capillary blood flow based on anatomic and distensibility data", *American Journal of Physiology—Heart and Circulatory Physiology*, Dec. 1, 1999, vol. 277 No. 6, p. H2158-H2166, and bibliography (1 page).

* cited by examiner

FIG. 4

111 UNSTRUCTURED GRID DATA

111a NODE INFORMATION TABLE

| NODE NUMBER | COORDINATE |
|---|---|
| 1 | 0.00 0.00 0.00 |
| 2 | 0.00 0.00 0.50 |
| ⋮ | ⋮ |
| $N_{nodes}$ | 1.00 2.00 3.00 |

111b ELEMENT INFORMATION TABLE

| ELEMENT NUMBER | NODE NUMBER |
|---|---|
| 1 | 1,2,3,4 |
| 2 | 2,3,4,5 |
| ⋮ | ⋮ |
| $N_{mesh}$ | $N_i, N_j, N_k, N_l$ |

FIG. 5

112 CORONARY CIRCULATION MACRO MODEL

112a NODE INFORMATION TABLE

| NODE NUMBER | COORDINATE |
|---|---|
| 1 | 0.00 0.00 0.00 |
| 2 | 0.00 0.00 0.50 |
| ⋮ | ⋮ |
| $N_{nodes}$ | 1.00 2.00 3.00 |

112b BLOOD VESSEL ELEMENT INFORMATION TABLE

| ELEMENT NUMBER | NODE | LEVEL | DIAMETER | CONDUCTANCE |
|---|---|---|---|---|
| 1 | 1,2 | 11 | 0.0015 | 7.6E-05 |
| 2 | 2,3 | 11 | 0.0014 | 7.0E-05 |
| ⋮ | ⋮ | ⋮ | ⋮ | ⋮ |
| $N_{elem}$ | $N_{nodes}-1, N_{nodes}$ | 6 | 0.0001 | 5.0E-11 |

FIG. 6

113 CORONARY CIRCULATION MICRO MODEL

113a NODE INFORMATION TABLE

| NODE NUMBER | COORDINATE |
|---|---|
| 1 | 0.00 0.00 0.00 |
| 2 | 0.00 0.00 0.50 |
| ... | ... |
| $N_{nodes}$ | 1.00 2.00 3.00 |

113b BLOOD VESSEL ELEMENT INFORMATION TABLE

| ELEMENT NUMBER | NODE | LEVEL | LENGTH | DIAMETER | VASCULAR WALL ELASTIC MODULUS | STANDARD PRESSURE DIFFERENCE | NUMBER |
|---|---|---|---|---|---|---|---|
| 1 | 1,2 | 5 | 4.5E−4 | 7.1E−5 | 9.7E−10 | 1.0E+4 | 1 |
| 2 | 2,3 | 4 | 1.12E−4 | 4.2E−5 | 4.6E−09 | 9.5E+4 | 8 |
| ... | ... | ... | ... | ... | ... | ... | ... |
| $N_{elem}$ | $N_{nodes}-1, N_{nodes}$ | 1 | 6.0E−5 | 6.5E−6 | 2.6E−09 | 3.0E+04 | 128 |

VISUALIZATION APPARATUS AND VISUALIZATION METHOD

CROSS-REFERENCE TO RELATED APPLICATION

This application is based upon and claims the benefit of priority of the prior Japanese Patent Application No. 2014-146637, filed on Jul. 17, 2014, the entire contents of which are incorporated herein by reference.

FIELD

The embodiments discussed herein relate to a visualization apparatus and a visualization method for visualizing a simulation result.

BACKGROUND

In the field of high performance computing, living body simulation is performed to numerically analyze a phenomenon that occurs in an organ, such as a heart. For example, simulation using a computer, such as a supercomputer, reproduces the behavior of cardiac muscle and displays the behavior of a heart using a three dimensional computer graphics technology. Also, simulation is also performed for coronary circulation associated with the behavior of the cardiac muscle.

The coronary circulation is a vascular network (hereinafter, referred to as "coronary circulation network") that supplies blood to cardiac muscle of a heart. The coronary circulation network for supplying blood to cardiac muscle includes a coronary artery for transporting blood from a Valsalva sinus, and a coronary vein for transporting carbon dioxide that is ejected from the cardiac muscle that has consumed oxygen. The coronary circulation network ranges from a blood vessel having a diameter confirmable as an organ to a blood vessel having a diameter for circulating blood into cardiac muscle. The research for anatomically figuring out the entire structure of the vascular network is proceeding. For example, there is a literature relevant to hemodynamic analysis of coronary capillary.

If coronary circulation is simulated using a three-dimensional model corresponding to a heart of a patient, a patient-specific coronary circulation is reproduced by a computer. Thus, the technology for creating a three-dimensional model specific to a patient is being studied. For example, there is a study on the technology for creating a three-dimensional model representing at least a part of a patient's heart, on the basis of patient-specific data relevant to the geometry of the patient's heart. Also, there is a study on the technology for generating a 3D model of a heart and cardiac blood vessels, using the data generated from a plurality of tomographic images of a body including a heart. Further, there is also a study on the technology for calculating the motion of a three dimensional shape, using pictures of a moving object, such as a heart, which is taken from a plurality of directions.

Note that, if coronary circulation including a narrow vascular network is simulated, the processing load of a computer becomes very large. Thus, the technology for efficiently simulating coronary circulation including a narrow vascular network is being studied.

See, for example, International Publication Pamphlet No. WO 2012/021307, Japanese Laid-open Patent Publication Nos. 2011-200549, 2004-201730, and 2013-233369. Also, see Ghassan S. Kassab et al., "A hemodynamic analysis of coronary capillary blood flow based on anatomic and distensibility data", American Journal of Physiology—Heart and Circulatory Physiology, 1 Dec. 1999, Vol. 277 No. 6 H2158-H2166.

In order to observe a simulation result of a heart using a three-dimensional model, the simulation result is displayed on the three-dimensional model. For example, the simulation result is observed on a three-dimensional model by displaying the three-dimensional model in such a manner that a difference between values of physical quantities of cardiac muscle and blood vessel estimated by the simulation is replaced by a difference between colors.

However, the vascular network of the microcirculatory system is defined only in a two-dimensional flat structure, and the simulation result of the microcirculatory system is unable to be confirmed on a three-dimensional structure. That is, from the view point of simulation of blood flow such as coronary circulation, a sufficiently accurate simulation result is obtained with respect to the microcirculatory system including narrow blood vessels, such as blood capillary, without creating a three dimensional model. Hence, with respect to the microcirculatory system, the model of the vascular network used in the simulation defines a structure, such as a diameter, a length, and a connection relationship, of blood vessels on a two-dimensional plane, and does not define a three-dimensional structure. As a result, a three-dimensional structure of the microcirculatory system is not reproduced, and a simulation result of the microcirculatory system is unable to be observed on a three-dimensional structure.

SUMMARY

According to one aspect, there is provided a visualization apparatus including: a memory configured to store a circulation model in which a vascular network, of an organ, having a diameter equal to or smaller than a predetermined value is defined on a two-dimensional plane, and a simulation result of a blood flow in the vascular network of the circulation model; and a processor configured to perform a procedure including: transforming the circulation model into a three-dimensional structure including the vascular network located on a cylindrical surface of a cylinder, and displaying the simulation result on the three-dimensional structure.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 4 illustrates an example of unstructured grid data;

FIG. 5 illustrates an example of a data structure of a macro model of coronary circulation;

FIG. 6 illustrates an example of a data structure of a micro model of coronary circulation;

DESCRIPTION OF EMBODIMENTS

Figure 1:
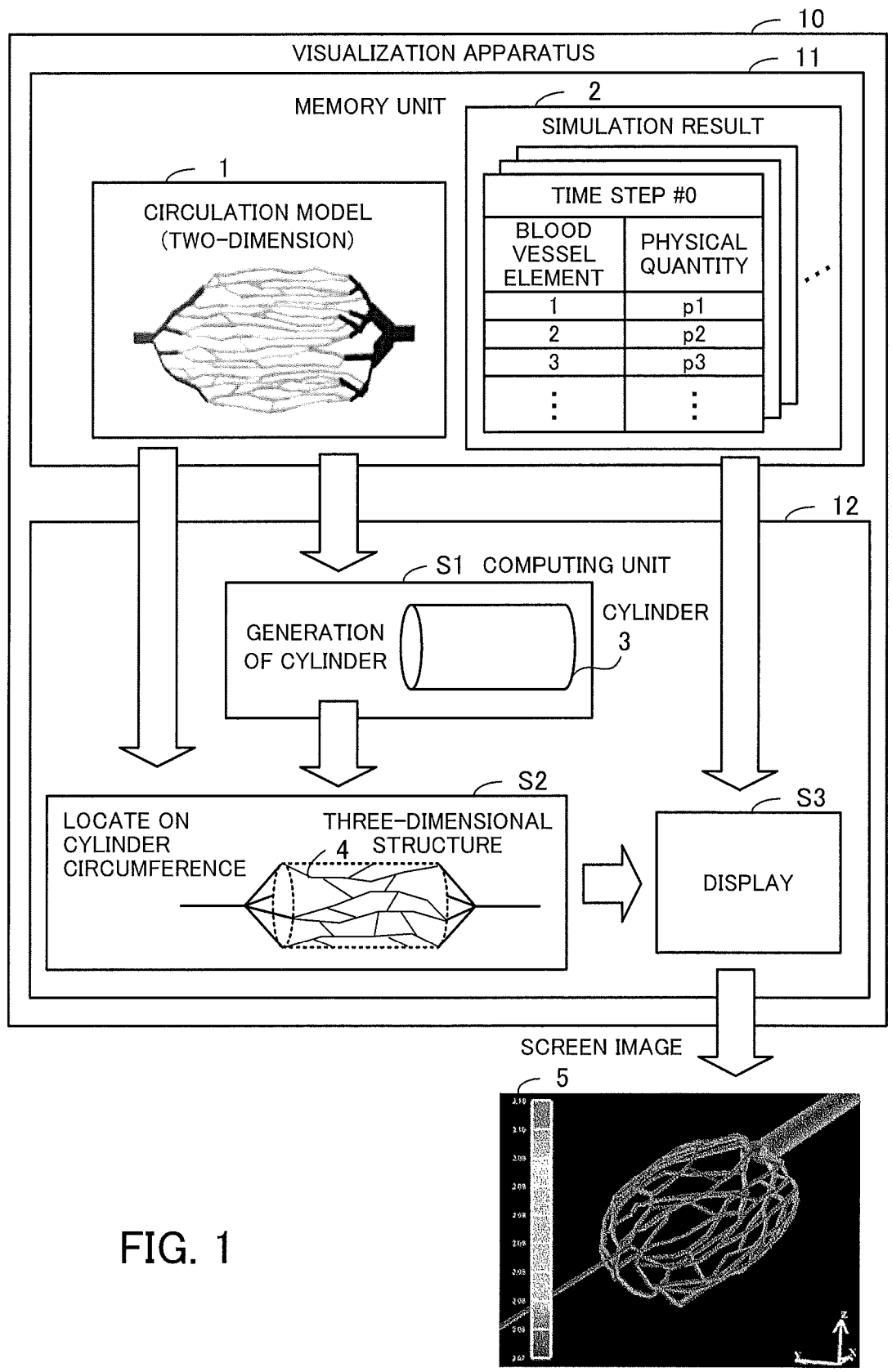
FIG. 1 illustrates an exemplary function and configuration of an apparatus according to a first embodiment.

Several embodiments will be described below with reference to the accompanying drawings, wherein like reference numerals refer to like elements throughout. Note that each embodiment may be combined with another embodiment or other embodiments unless the combined embodiments contradict each other.

First Embodiment

First, the first embodiment will be described. In the first embodiment, a simulation result of blood flow of a microcirculatory system is displayed on a three dimensional vascular network model, so that a user can view the result easily.

FIG. 1 illustrates an exemplary function and configuration of an apparatus according to the first embodiment. A visualization apparatus 10 includes a memory unit 11 and a computing unit 12.

The memory unit 11 stores a circulation model 1 in which a vascular network, of an organ, having a diameter equal to or smaller than a predetermined value is defined on a two-dimensional plane, and a simulation result 2 of blood flow in the vascular network defined in the circulation model 1. The organ is a heart, for example. The circulation model 1 is a microcirculation model of structures of arterioles, venules, and blood capillaries between the arterioles and the venules, for example. The simulation result 2 indicates physical quantities in a blood vessel element of each time step in the simulation, for example. The physical quantities is, for example, a pressure in the blood vessel, and an oxygen concentration or a carbon dioxide concentration of blood that flows in the blood vessel.

The computing unit 12 transforms the circulation model 1 into a three-dimensional structure 4 in which a vascular network is located on a cylindrical surface of a cylinder 3, and displays the simulation result 2 on the three-dimensional structure. For example, the computing unit 12 creates a cylinder 3 having a cylindrical surface of a circumferential length that is equal to the width of the circulation model 1 in the orthogonal direction to the blood flow direction from artery side to vein side (step S1). Thereafter, the computing unit 12 locates blood capillaries on the cylinder 3 (step S2). For example, the computing unit 12 locates the vascular network representing the structure of the blood capillaries on the cylindrical surface of the cylinder 3. Thereby, the circulation model is transformed into a three-dimensional structure 4. Then, the computing unit 12 displays the simulation result 2 on the three-dimensional structure 4 which is transformed from the circulation model 1 (step S3). Here, the cylinder 3 is not displayed. For example, the computing unit 12 colors the surface of the three-dimensional structure of the microcirculatory system with colors according to physical quantities of the blood vessel or the blood flow in the blood vessel, in order to display the three-dimensional structure on the screen 5.

In this way, the two-dimensional circulation model used in the simulation is transformed into a three-dimensional structure, to display a simulation result on the three-dimensional structure. As a result, one can easily observe the simulation result on the three-dimensional structure.

Note that the computing unit 12 is configured by a processor in the visualization apparatus 10, for example. Also, the memory unit 11 is configured by a memory included in the visualization apparatus 10, for example. Further, the lines that connect between the elements in FIG. 1 illustrate part of communication channels, and communication channels other than the depicted communication channels are also usable.

Second Embodiment

Next, the second embodiment will be described. In simulation of an entire heart is performed to make its simulation result observable on a model of a three-dimensional structure, including a microcirculatory system of coronary circulation.

Figure 2:
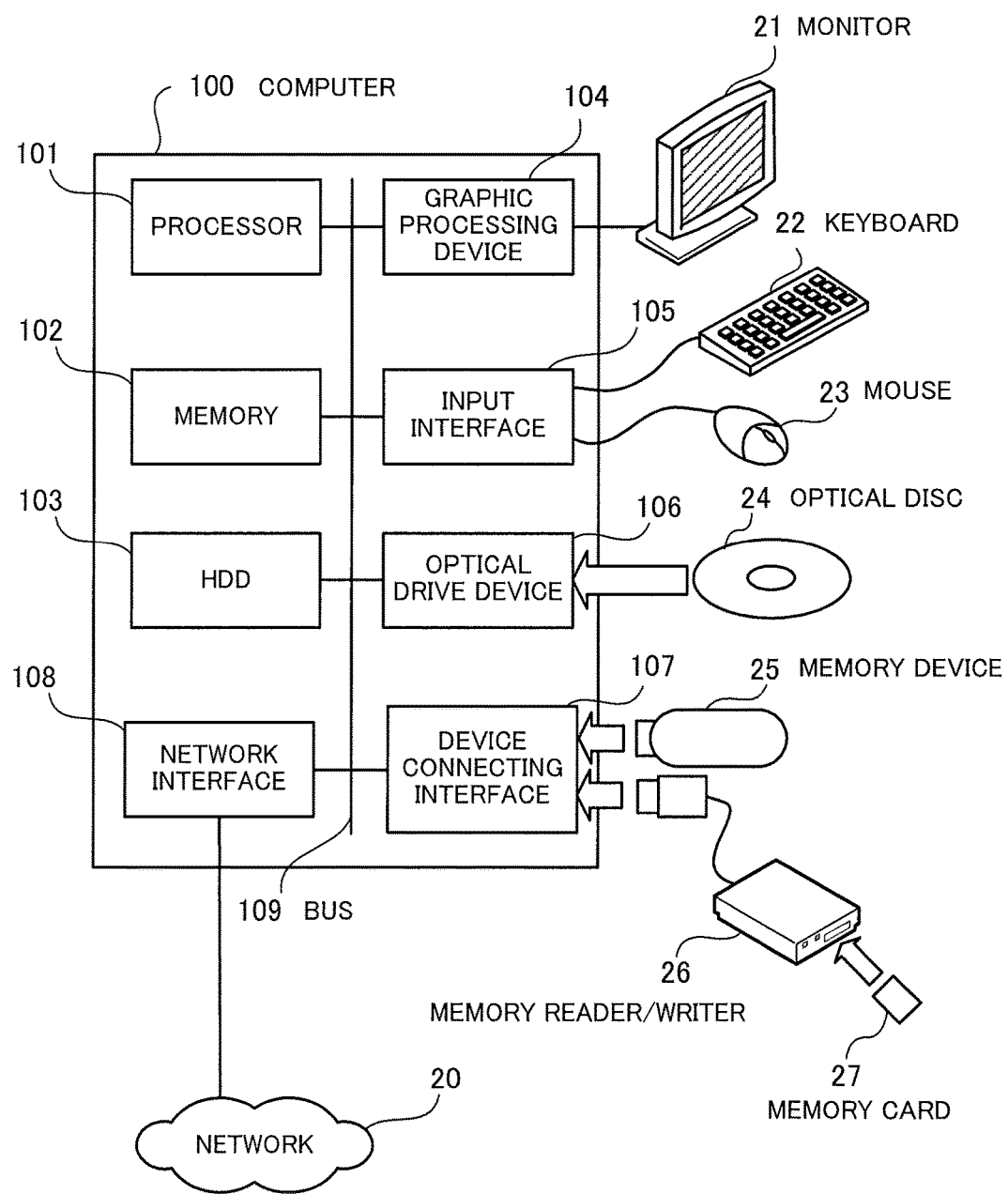
FIG. 2 illustrates an exemplary configuration of a hardware of a computer used in the present embodiment.

FIG. 2 illustrates an exemplary configuration of a hardware of a computer used in the present embodiment. Each device of the computer 100 is controlled by a processor 101. The processor 101 is connected to a memory 102 and a plurality of peripheral devices via a bus 109. The processor 101 may be a multiprocessor. The processor 101 is, for example, a central processing unit (CPU), a micro processing unit (MPU), or a digital signal processor (DSP). At least a part of functions implemented by executing programs in the processor 101 may be configured by an electronic circuit, such as an application specific integrated circuit (ASIC) or a programmable logic device (PLD).

The memory 102 is used as a main memory device of the computer 100. In the memory 102, at least a part of OS (Operating System) programs and application programs is temporarily stored to be executed by the processor 101. Also, the memory 102 stores various types of data used in processing by the processor 101. The memory 102 is, for example, a volatile semiconductor memory device, such as a random access memory (RAM).

The peripheral devices connected to the bus 109 include a hard disk drive (HDD) 103, a graphic processing device 104, an input interface 105, an optical drive device 106, a device connecting interface 107, and a network interface 108.

The HDD 103 magnetically writes data into, and reads data from, a built-in disk. The HDD 103 is used as an auxiliary memory device of the computer 100. The HDD 103 stores OS programs, application programs, and various types of data. Note that the auxiliary memory device may be a non-volatile semiconductor memory device, such as a flash memory.

The graphic processing device 104 is connected to a monitor 21. The graphic processing device 104 displays an image on a screen of the monitor 21 in accordance with an instruction from the processor 101. The monitor 21 is, for example, a display device using a cathode ray tube (CRT), a liquid crystal display device, or the like.

The input interface 105 is connected to a keyboard 22 and a mouse 23. The input interface 105 transmits to the processor 101 a signal sent from the keyboard 22 and the mouse 23. Note that the mouse 23 is an example of pointing device, and other pointing devices may be used. Other pointing devices are, for example, a touch panel, a tablet, a touch pad, and a trackball.

The optical drive device 106 reads data recorded in an optical disc 24, using laser light or the like. The optical disc 24 is a portable storage medium in which data is recorded in a readable manner by reflection of light. The optical disc 24 is, for example, a DVD (Digital Versatile Disc), a DVD-RAM, a CD-ROM (Compact Disc Read Only Memory), or a CD-R(Recordable)/RW(ReWritable).

The device connecting interface 107 is a communication interface for connecting the peripheral devices to the computer 100. For example, the device connecting interface 107 is connected to a memory device 25 and a memory reader/writer 26. The memory device 25 is a storage medium having a communication function with the device connecting interface 107. The memory reader/writer 26 is a device that writes data into a memory card 27 or reads data from the memory card 27. The memory card 27 is a storage medium of a card type.

The network interface 108 is connected to the network 20. The network interface 108 transmits data to, and receives data from, other computers or communication devices via the network 20.

The processing function of the second embodiment is implemented by the above hardware configuration. Note that the visualization apparatus 10 illustrated in the first embodiment is also configured by the same hardware as the computer 100 illustrated in FIG. 2.

The computer 100 implements the processing function of the second embodiment, by executing a program stored in a computer-readable storage medium, for example. The program describing a procedure executed by the computer 100 may be stored in various storage media. For example, the program executed by the computer 100 may be stored in the HDD 103. The processor 101 loads at least a part of program into the memory 102 from the HDD 103, and executes the program. Also, the program executed by the computer 100 may be stored in a portable storage medium, such as the optical disc 24, the memory device 25, and the memory card 27. The program stored in the portable storage medium is executable after installed in the HDD 103, by the control from the processor 101, for example. Also, the processor 101 may read a program directly from a portable storage medium to execute the program.

Figure 3:
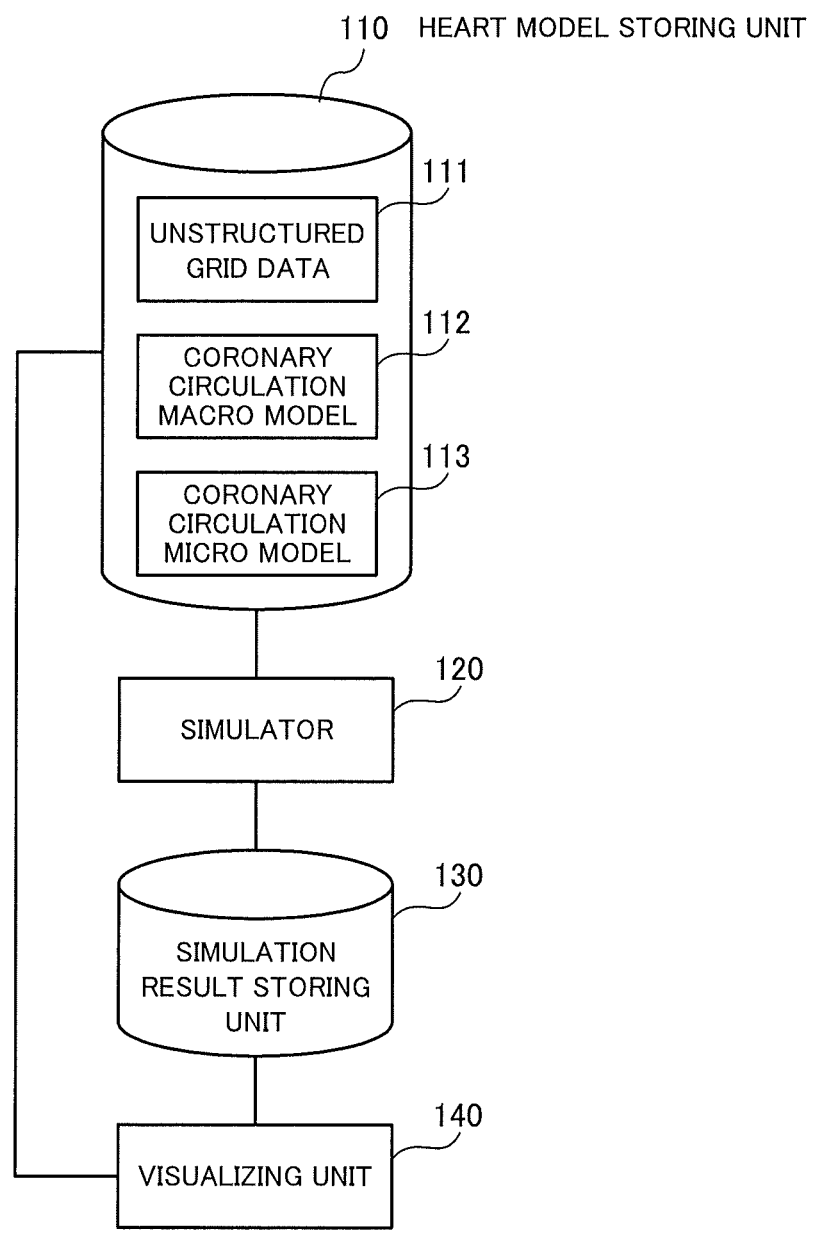
FIG. 3 is a block diagram of a function of a computer according to a second embodiment.

FIG. 3 is a block diagram of functions of the computer according to the second embodiment. The computer 100 includes a heart model storing unit 110, a simulator 120, a simulation result storing unit 130, and a visualizing unit 140.

The heart model storing unit 110 stores data that defines cardiac muscle of a heart and a shape of blood vessels. For example, data indicating the heart of a patient is stored in the heart model storing unit 110. In the heart model storing unit 110, unstructured grid data 111, a coronary circulation macro model 112, and a coronary circulation micro model 113 are stored. For example, a part of a storage region of the memory 102 or the HDD 103 is used as the heart model storing unit 110.

The unstructured grid data 111 is data that represents the shape of a heart three-dimensionally. In the unstructured grid data 111, a plurality of tetrahedral elements represent the shape of the heart, for example. In that case, a large number of nodes are provided in a space the heart exists. Then, a large number of tetrahedrons each having four nodes at their apexes are defined. One tetrahedron is an element representing a cardiac muscle cell of the heart, for example.

The coronary circulation macro model 112 is data representing the three-dimensional structure of blood vessels having a diameter equal to or larger than a predetermined value in the coronary circulation system of the heart. The coronary circulation micro model 113 is data representing the two-dimensional structure of blood vessels having a diameter smaller than the predetermined value in the coronary circulation system of the heart.

The simulator 120 simulates the behavior of the heart, including heartbeat, on the basis of the three-dimensional model of the heart. Also, the simulator 120 simulates the blood flow (coronary circulation) in the heart. Then, the simulator 120 stores a simulation result in the simulation result storing unit 130. For example, the simulator 120 increments the time (time step) by a predetermined time period in the simulation and, at each incremented time, calculates the positions of nodes of the three-dimensional model, and physical quantities (for example, blood pressure and blood flow rate) of the elements and the nodes. The positions and the physical quantities of the nodes at each time are calculated on the basis of the positions and the physical quantities of the nodes at the previous time. The simulator 120 outputs the positions of the nodes and the physical quantities of the elements and the nodes at a predetermined time in the timeline during the simulation, as a simulation result.

The simulation result storing unit 130 stores the simulation result. For example, a part of the storage region of the memory 102 or the HDD 103 is used as the simulation result storing unit 130.

The visualizing unit 140 displays the behavior and the coronary circulation system of the heart on the monitor 21. For example, the visualizing unit 140 transforms the coronary circulation micro model 113 into a geometric shape based on medical knowledge, so that even the microvascular network is correctly displayed three-dimensionally. Further, the visualizing unit 140 sets various types of physical quantities, such as blood flow and blood pressure, in the blood vessels of the coronary circulation macro model 112 and the coronary circulation micro model 113. Then, the visualizing unit 140 displays the cardiac muscle of the heart or the blood vessels of the coronary circulation system, with the color according to the values of the set physical quantities, for example.

Note that the visualizing unit 140 is an example of the computing unit 12 in the first embodiment illustrated in FIG. 1. Also, the function of a combination of the heart model storing unit 110 and the simulation result storing unit 130 is an example of the memory unit 11 in the first embodiment illustrated in FIG. 1. Note that the lines that connect between the elements in FIG. 3 illustrate part of communication channels, and communication channels other than the depicted communication channels are also usable. Also, the function of each element illustrated in FIG. 3 is implemented by causing a computer to execute a program module corresponding to the element, for example.

Next, data in the heart model storing unit 110 will be described in detail. FIG. 4 illustrates an example of the unstructured grid data. The unstructured grid data 111 includes a node information table 111a and an element information table 111b, for example. In other words, the node information table 111a and the element information table 111b forms the unstructured grid data. In the node information table 111a, a node number and coordinates indicating the position of a node are set for each node. Note that the coordinates of each node set in the node information table 111a indicate the position of a node before starting the simulation, and the position of the node changes when heartbeat is reproduced by the simulation. In the element information table 111b, an element number and node numbers of nodes that forms apexes of a tetrahedral element are set for each element. A three-dimensional model of a heart is generated on the basis of the data stored in the unstructured grid data 111 illustrated in FIG. 4.

FIG. 5 illustrates an example of a data structure of the macro model of the coronary circulation. The coronary circulation macro model 112 is the information indicating a structure of thick coronary arteries and veins in a vascular network of a heart. The coronary circulation macro model 112 includes a node information table 112a and a blood vessel element information table 112b. The structure of the node information table 112a is same as the structure of the node information table 111a of the unstructured grid data 111 illustrated in FIG. 4.

In the blood vessel element information table 112b, nodes, a level, a diameter, and a conductance are set in association with each element number of blood vessel element. The element number is an identification number for uniquely identifying a blood vessel element. The node includes identification numbers of nodes at both ends of a blood vessel element. The level indicates the thickness of a blood vessel. The level of an artery is a positive value, and the level of a vein is a negative value. The blood capillary has the smallest absolute value of the level, and the level increases as the blood vessel becomes thicker. The diameter is a diameter of a blood vessel. The conductance is a numerical value indicating flowability of blood in a blood vessel. As the conductance becomes larger, the resistance in the blood vessel becomes smaller, facilitating the blood flow. Note that Nelem indicates the number of elements of the blood vessels.

FIG. 6 illustrates an example of a data structure of the micro model of the coronary circulation. The coronary circulation micro model 113 is the information indicating the structure of an intermediate network, arterioles, venules, and blood capillaries in the vascular network of the heart. The coronary circulation micro model 113 includes a node information table 113a and a blood vessel element information table 113b. The structure of the node information table 113a is same as the structure of the node information table 111a of the unstructured grid data 111 illustrated in FIG. 4.

In the blood vessel element information table 113b, nodes, a level, a length, a diameter, a vascular wall elastic modulus, a standard pressure difference, and number are set in association with each element number of a blood vessel element. The node includes identification numbers of nodes at both ends of a blood vessel element. The level is the level of the blood vessel. The length is the length of the blood vessel element. The diameter is the diameter of the blood vessel element. The vascular wall elastic modulus is the elastic modulus of the wall of the blood vessel element. The standard pressure difference indicates a standard value of pressure difference between blood pressure in blood vessel and intramyocardial pressure. The blood vessel diameter is calculated on the basis of this standard value and the pressure difference at each time in the simulation. The number is the number of elements of the same level when symmetry is assumed.

Figure 7:
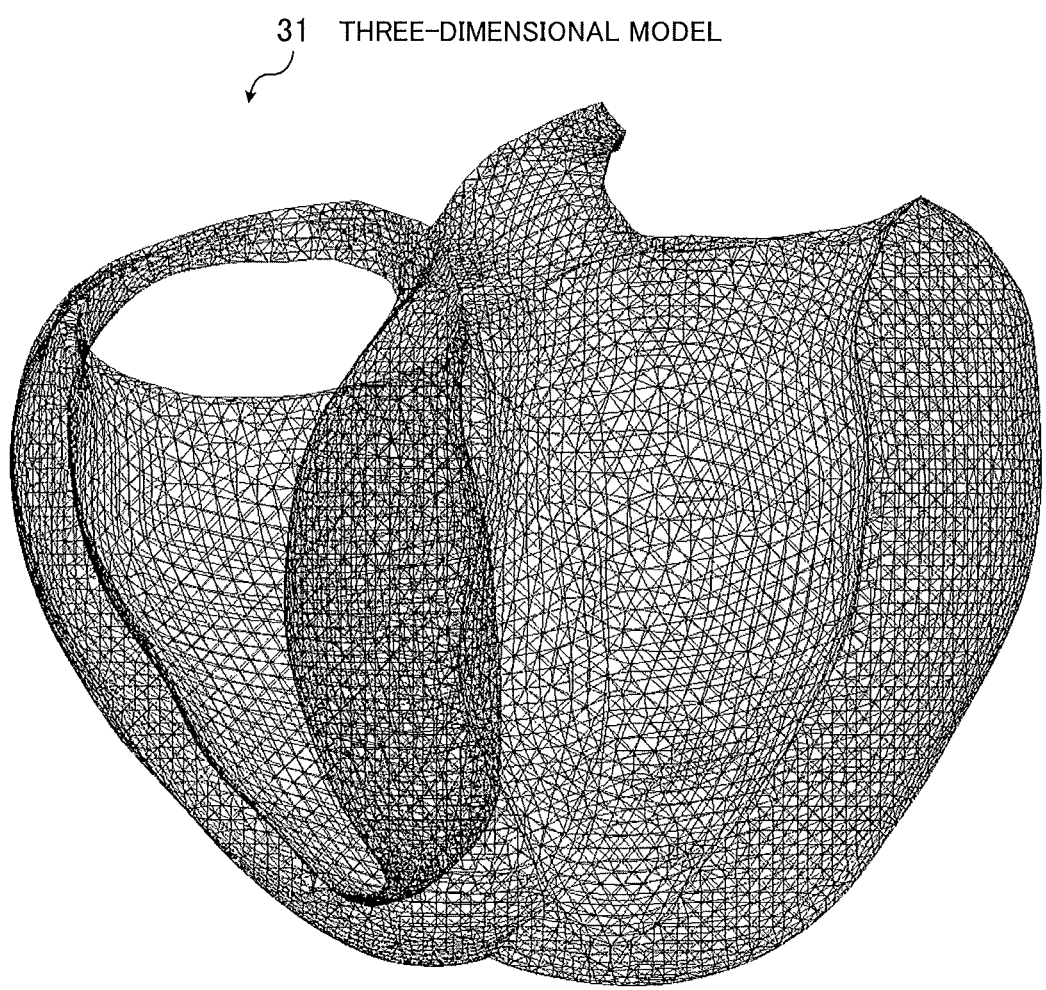
FIG. 7 illustrates an example of a three-dimensional model of a heart.

A three-dimensional model of a heart is generated on the basis of the above data for defining a heart model. FIG. 7 illustrates an example of a three-dimensional model of a heart. In the example of FIG. 7, a three-dimensional model 31 is an aggregation of tetrahedral elements. A simulation for reproducing a propagation situation (excitement propagation) of electrical signals via cardiac muscle of a heart is performed by inputting an initial condition of electrical signals to the three-dimensional model 31. Also, a simulation of a behavior of the heart is performed by inputting a condition relevant to action of contraction and extension of cardiac muscle to the three-dimensional model 31. Further, a simulation of blood flow in the coronary circulation system is performed simultaneously with the simulation of the behavior of the heart which is caused by contraction and extension of cardiac muscle. The simulation results are stored in the simulation result storing unit 130.

Figure 8:
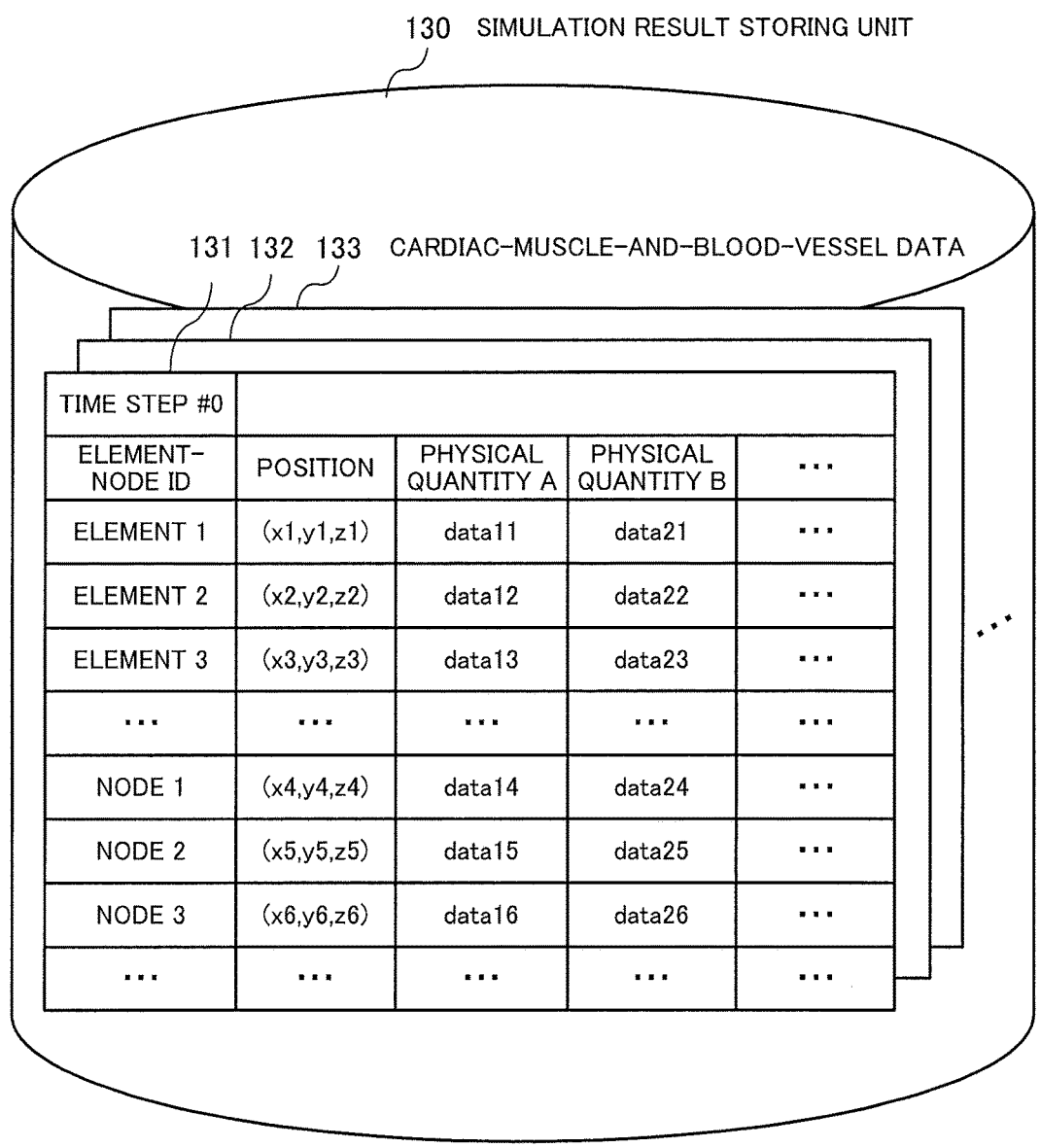
FIG. 8 illustrates an example of a data structure of a simulation result storing unit.

FIG. 8 illustrates an example of the data structure of the simulation result storing unit. In the simulation result storing unit 130, cardiac-muscle-and-blood-vessel data 131, 132, and 133 is stored for each time step, which is a time point at which one simulation result is recorded. The cardiac-muscle-and-blood-vessel data 131, 132, and 133 is information indicating a state (including a shape) of a heart at a time step. A number (time step index) of time step is given to each cardiac-muscle-and-blood-vessel data 131, 132, and 133.

For example, in the cardiac-muscle-and-blood-vessel data 131, 132, and 133, a position and values of various physical quantities of an element or a node are set in association with each element-node ID. The shape of the heart at each time step is decided, depending on positions of nodes at each time step. Note that, the position of an element is the gravity center position of a tetrahedral element, for example. Also, a value of one physical quantity may be set in both of element and node, or may be set only one of element and node. The physical quantities are, for example, a pressure on a blood vessel, and an oxygen concentration or a carbon dioxide concentration in blood that flows in a blood vessel.

Figure 9:
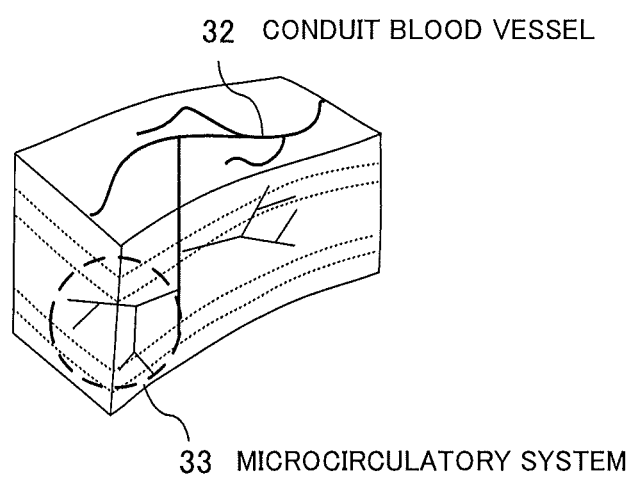
FIG. 9 illustrates an example of narrow blood vessels.

Next, the coronary circulation system will be described. In the coronary circulation system, an aorta and a vena cava branch into narrower blood vessels. FIG. 9 illustrates an example of narrower blood vessels. If the diameter of a blood vessel is several ten μm to several mm, the blood vessel is a conduit blood vessel 32. The conduit blood vessel 32 transports blood throughout the heart. The conduit blood vessel 32 branches into blood vessels (delivering vessels) running to the direction that penetrates the wall of the heart, from a blood vessel (distributing vessel) running on heart surface.

The blood vessel extending in the direction that penetrates the wall of the heart further branches into other blood vessels that form the microcirculatory system 33. The microcirculatory system 33 includes arterioles, venules, and blood capillaries each having a diameter of several ten μm. The conduit blood vessel 32 has a tree-like structure, while the microcirculatory system 33 has a net-like structure. The microcirculatory system 33 supplies nutrients to cardiac muscle. The structure of the coronary circulation system is modeled, including these narrow blood vessels.

Figure 10:
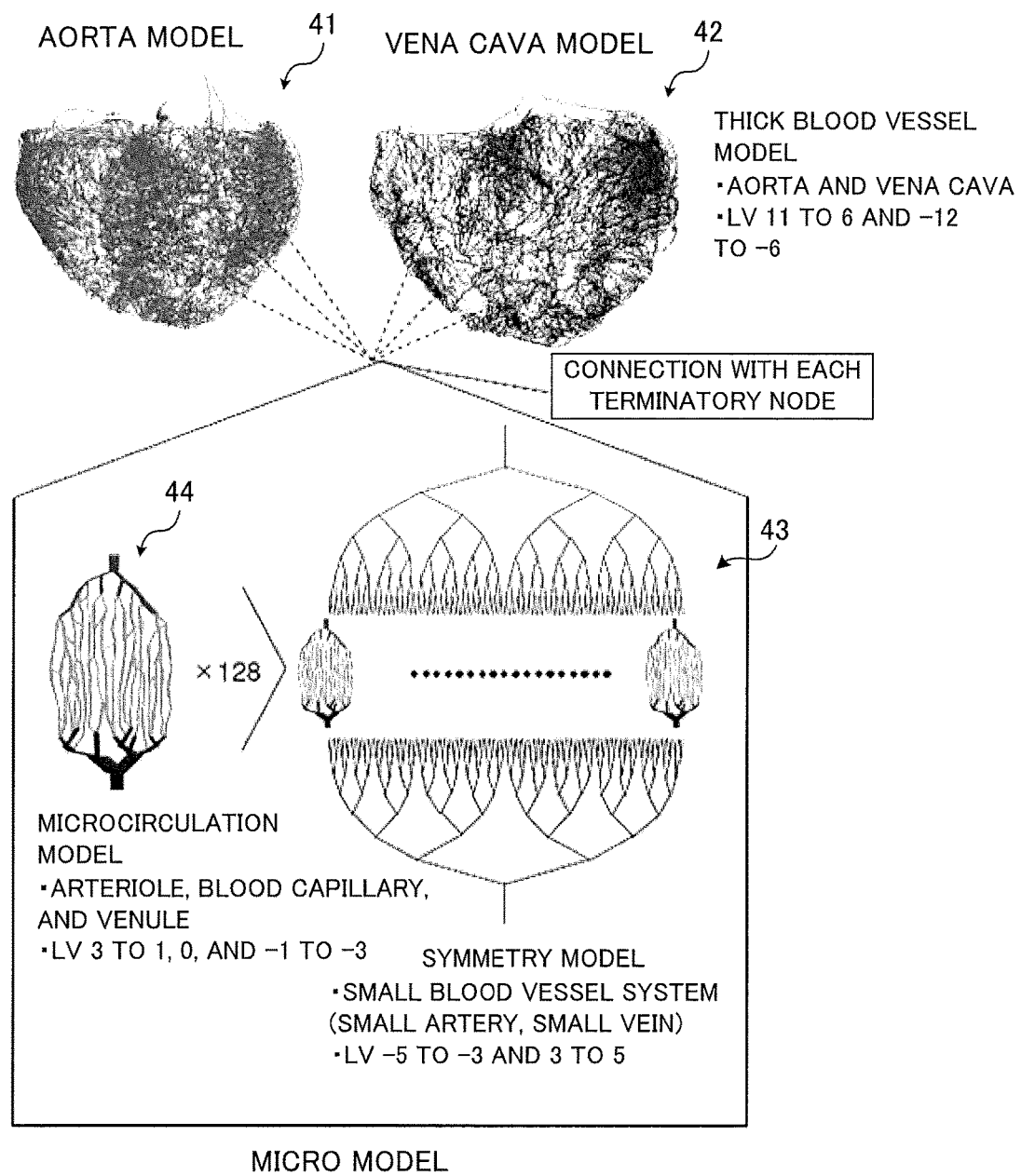
FIG. 10 illustrates an example of a model of a coronary circulation system.

FIG. 10 illustrates an example of a model of the coronary circulation system. In the coronary circulation macro model 112, structures of an aorta model 41 and a vena cava model 42 are defined. The aorta model 41 and the vena cava model 42 include blood vessels of a diameter within the ranges of level 11 to 6 and −12 to −6.

The terminatory node between the aorta model 41 and the vena cava model 42 includes a symmetry model 43 in the coronary circulation micro model 113. The symmetry model 43 represents a small blood vessel system, and is defined to locate small arteries and small veins symmetrically. The symmetry model 43 includes blood vessels of a diameter within ranges of level −5 to −3 and 3 to 5.

Also, in the coronary circulation micro model 113, microcirculation models 44 are defined between the small arteries and the small veins of the symmetry model 43. For example, one hundred twenty eight microcirculation models 44 are located between the small arteries and the small veins of the symmetry model 43. The microcirculation model 44 represents the structure of arterioles, blood capillaries, and venules. The microcirculation model 44 includes blood vessels of a diameter within ranges of level 3 to 1, 0, and −1 to −3.

With respect to the aorta model 41 and the vena cava model 42, the structure of the coronary circulation is defined three-dimensionally based on medical knowledge in the model of coronary circulation system illustrated in FIG. 10. On the other hand, connection relationship, thickness, length, and the like of the blood vessel are defined two-dimensionally with respect to the symmetry model 43 and the microcirculation model 44, and their three-dimensional structures are not the real structure. Hence, if the coronary circulation simulation is used to calculate simulation results, such as blood flow distribution, of the micro region, and the coronary circulation micro model 113 is reproduced as it is to make the simulation results observable in the three-dimensional model, the coronary circulation micro model 113 would have an unnatural structure. Thus, in the second embodiment, when displaying the simulation results using the three-dimensional model, the visualizing unit 140 reconstructs the coronary circulation micro model 113 into a three dimensional structure based on medical knowledge.

Figure 11:
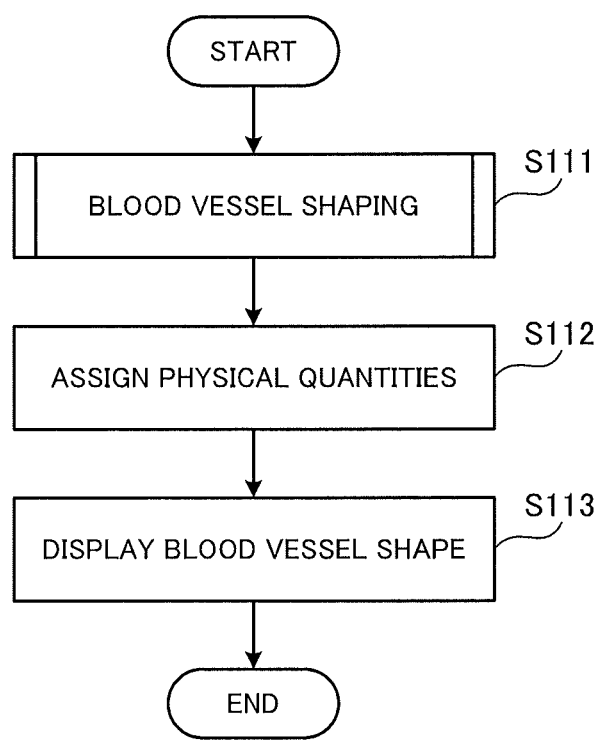
FIG. 11 is a flowchart illustrating an example of a procedure of a microscopic region visualizing process.

In the following, the procedure of a microscopic region visualizing process will be described. FIG. 11 is a flowchart illustrating an example of the procedure of the microscopic region visualizing process. Note that, the microscopic region visualizing process is executed in response to a visualization instruction from a user.

[Step S111] The visualizing unit 140 creates a geometric shape of blood vessels based on medical knowledge, on the basis of the coronary circulation micro model 113. The detail of this process will be described later (refer to FIG. 12).

[Step S112] The visualizing unit 140 assigns physical quantities to be visualized, to the blood vessels. For example, the visualizing unit 140 acquires the physical quantities to be visualized, from the simulation result storing unit 130. Then, the visualizing unit 140 assigns the acquired physical quantities, to the vascular network of the geometric shape created in step S111. The physical quantities to be visualized are selected by the input from a user, for example. The physical quantities to be visualized are, for example, a blood flow rate and a blood pressure.

[Step S113] The visualizing unit 140 colors the created three dimensional blood vessel shape with colors according to the set physical quantity values, and displays it on the monitor 21.

Figure 12:
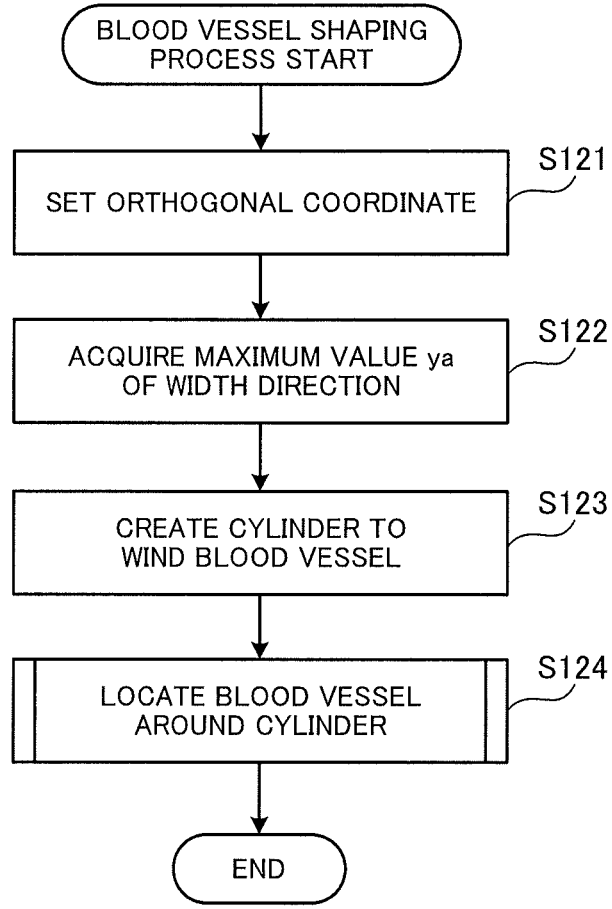
FIG. 12 is a flowchart illustrating an example of a procedure of a blood vessel shaping process.

Next, a blood vessel shaping process will be described in detail. FIG. 12 is a flowchart illustrating an example of the procedure of the blood vessel shaping process.

[Step S121] The visualizing unit 140 defines an orthogonal coordinate system to create a geometric shape of the coronary circulation micro model.

[Step S122] The visualizing unit 140 acquires the maximum value ya of the microcirculation model in the width direction.

Figure 13:
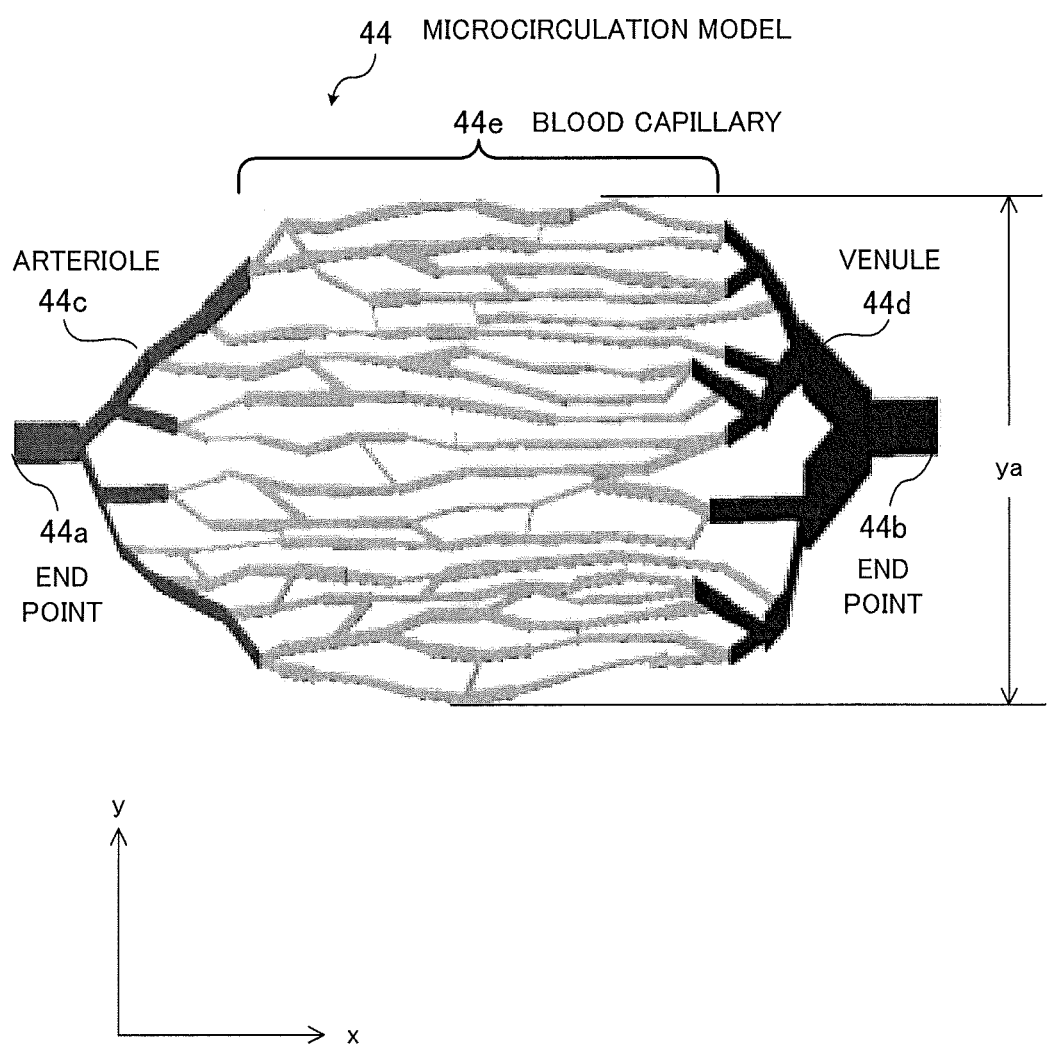
FIG. 13 is an enlarged view of a microcirculation model.

FIG. 13 is an enlarged view of the microcirculation model. In FIG. 13, arterioles 44c extend ramally from an end point 44a of left side. Also, venules 44d extend ramally from an end point 44b of right side. The arterioles 44c and the venules 44d are connected by net-like blood capillaries 44e. Here, x axis extends in the direction from the end point 44a to the end point 44b, and y axis extends in the orthogonal direction to x axis. The microcirculation model 44 is formed on x-y plane. In this case, the maximum value ya of the microcirculation model 44 in the width direction is the width of the microcirculation model 44 in y direction. The ya is approximately 200 μm, for example. Also, the width of the blood capillaries 44e in x direction is approximately 500 μm. The following description returns to FIG. 12.

[Step S123] The visualizing unit 140 creates a cylinder to wind the blood vessels. For example, the visualizing unit 140 creates a cylinder of a size in which the width of the microcirculation model 44 is equal to the cylinder circumferential length. In that case, a cylindrical diameter d is "d=ya/n" (n is the ratio of the circumference of a circle to its diameter). Also, the visualizing unit 140 sets a length of the cylinder at a same value as the distance between both ends of the blood capillaries 44e of the microcirculation model 44, for example. Also, the length of the cylinder may be set at a large value. For example, the visualizing unit 140 may sets the length of the cylinder at a same value as the distance between both end points 44a and 44b of the microcirculation model 44.

[Step S124] The visualizing unit 140 locates the blood vessels on the cylinder circumference. Here, the visualizing unit 140 elongates the blood vessels to locate them on the cylindrical inner surface, and then allows the blood vessels to shrink to its original length.

Figure 14:
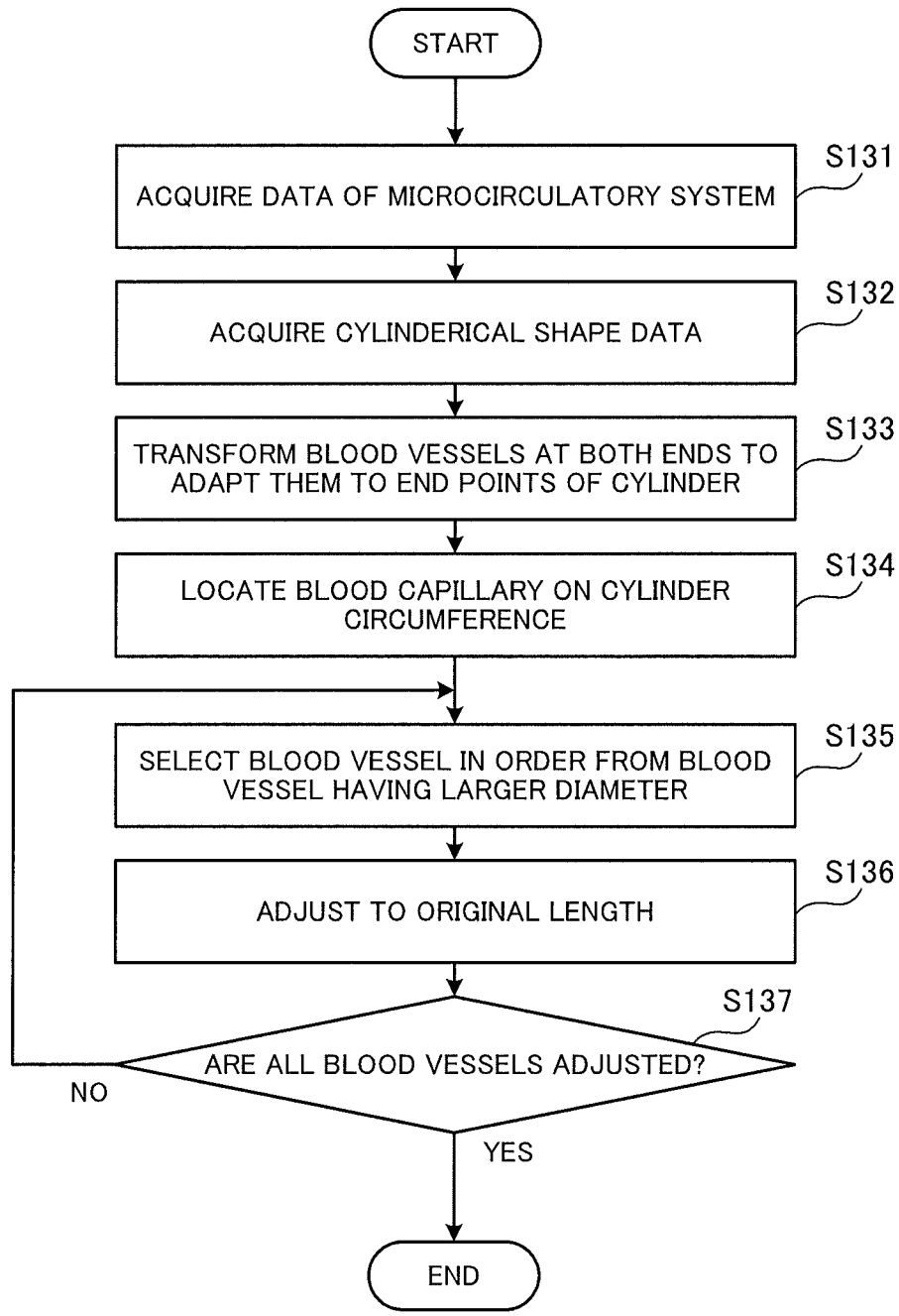
FIG. 14 is a flowchart illustrating an example of a procedure of a blood vessel locating process for locating blood vessels on a cylinder circumference.

FIG. 14 is a flowchart illustrating an example of a procedure of a blood vessel locating process for locating the blood vessels on the cylinder circumference.

[Step S131] The visualizing unit 140 acquires data of the microcirculatory system.

[Step S132] The visualizing unit 140 acquires data indicating a cylindrical shape.

[Step S133] The visualizing unit 140 transforms the blood vessels at the both ends of the microcirculatory system, to adapt them to the end points of the cylinder.

Figure 15:
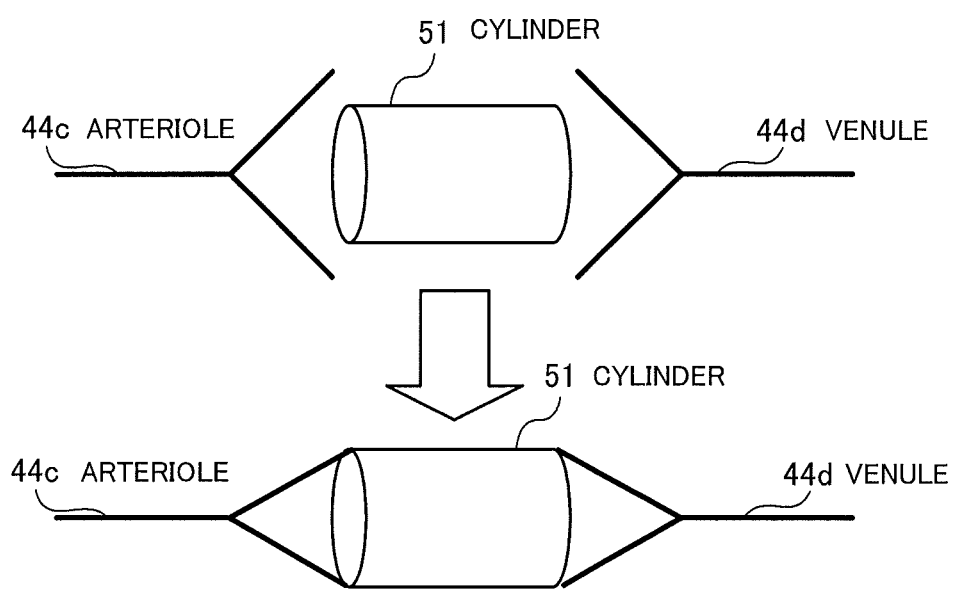
FIG. 15 illustrates an exemplary variant of a blood vessel at both ends of a microcirculatory system.

FIG. 15 illustrates an exemplary variant of the blood vessels at both ends of the microcirculatory system. Terminals (end portions connected to the blood capillaries) of the arteriole 44c and the venule 44d of the microcirculation model 44 are connected to end portions of the cylinder 51. The following description returns to FIG. 14.

[Step S134] The visualizing unit 140 locates the blood capillaries extending between the arteriole 44c and the venule 44d, on the cylinder circumference. Here, the length of each blood vessel is variable. For example, when the length of the cylinder is set at a large value, the visualizing unit 140 elongates the blood vessels and locates each blood vessel around the cylinder.

[Step S135] The visualizing unit 140 selects each blood vessel of the microcirculatory system, in order from a blood vessel having a larger diameter.

[Step S136] The visualizing unit 140 adjusts the selected blood vessel to its original length. For example, the visualizing unit 140 sets the diameter of the selected blood vessel at Ri, and the vector from an end portion connected to the thick blood vessel to the other end portion at vi. Then, the visualizing unit 140 fixes the end portion of the selected blood vessel which is connected to the thick blood vessel, and shrinks the length of the blood vessel back to its original length in the direction of the vector vi.

[Step S137] The visualizing unit 140 determines whether or not the lengths have been adjusted with respect to all blood vessels of the microcirculatory system. If the lengths of all blood vessel have been adjusted, the process ends. If there is any blood vessel for which the length has not been adjusted, the process proceeds to step S135.

As described above, if the length of each blood vessel is shrunk, the length of the cylinder is also shrunk accordingly. For example, the vector passing through the cylinder center in the longitudinal direction of the cylinder is assumed to be vector C. In this case, when the length of one blood vessel shortens by $\Delta vi$, the length of the cylinder shortens by $\Delta Li = \Delta vi (\cos \theta i)$. $\theta i$ is an angle formed by the vector vi and the vector C. The length of the cylinder is shortened by a cumulative value of the cylinder-shortening length $\Delta Li$ according to shrinkages of blood vessels, which exist on routes of blood vessels from one end to the other end of the microcirculatory system.

As the center portion of the microcirculation model is transformed into a cylindrical shape, the vascular network of the microcirculatory system is observed with a more real shape when displayed on a screen. For example, the visualizing unit 140 displays the microcirculation model with colors on the blood vessels, which are converted from the magnitudes of values of physical quantities in the simulation result of the coronary circulation. Here, an user selects physical quantities of an observation target, and then inputs information for specifying color mapping data indicating a correspondence relationship between values of the physical quantities and colors. The physical quantities of the observation target are, for example, pressure exerted on blood vessel, oxygen concentration of blood that flows in blood vessel, and carbon dioxide concentration of blood that flows in blood vessel.

Figure 16:
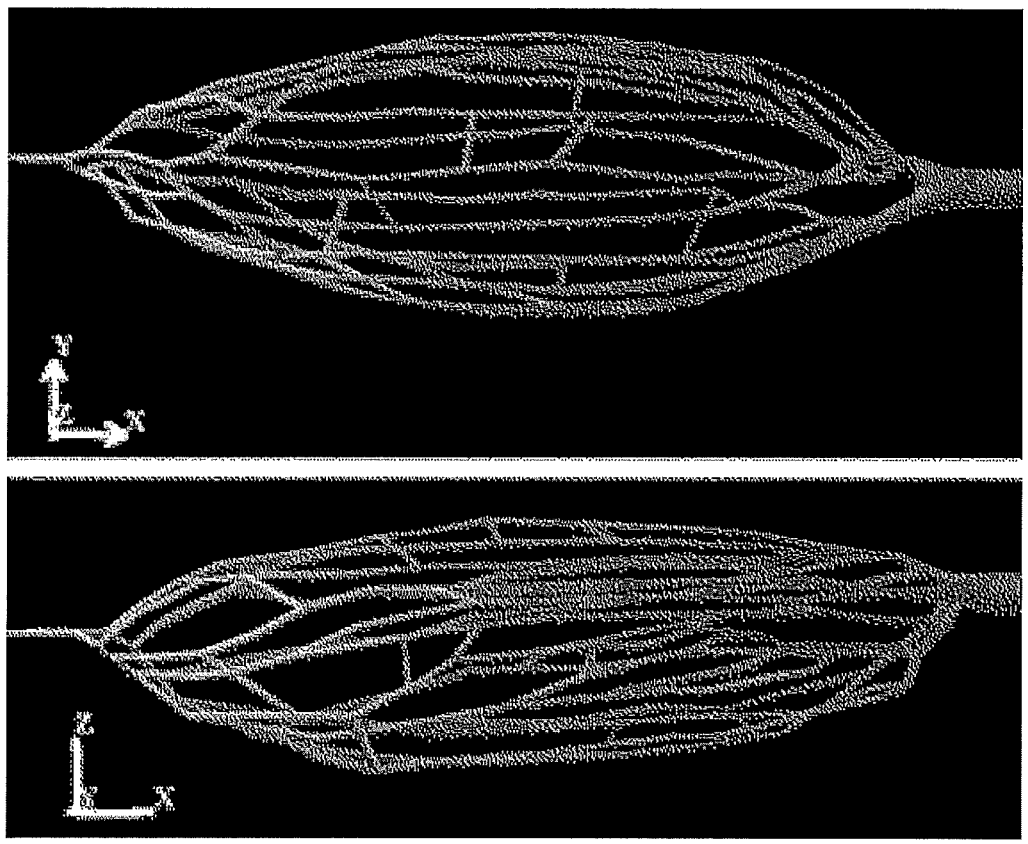
FIG. 16 illustrates a first exemplary display of a microcirculatory system.

FIG. 16 illustrates a first exemplary display of the microcirculatory system. In the upper side of FIG. 16, the microcirculatory system seen from Z axis direction is illustrated, and in the lower side the microcirculatory system seen from Y axis direction is illustrated.

Figure 17:
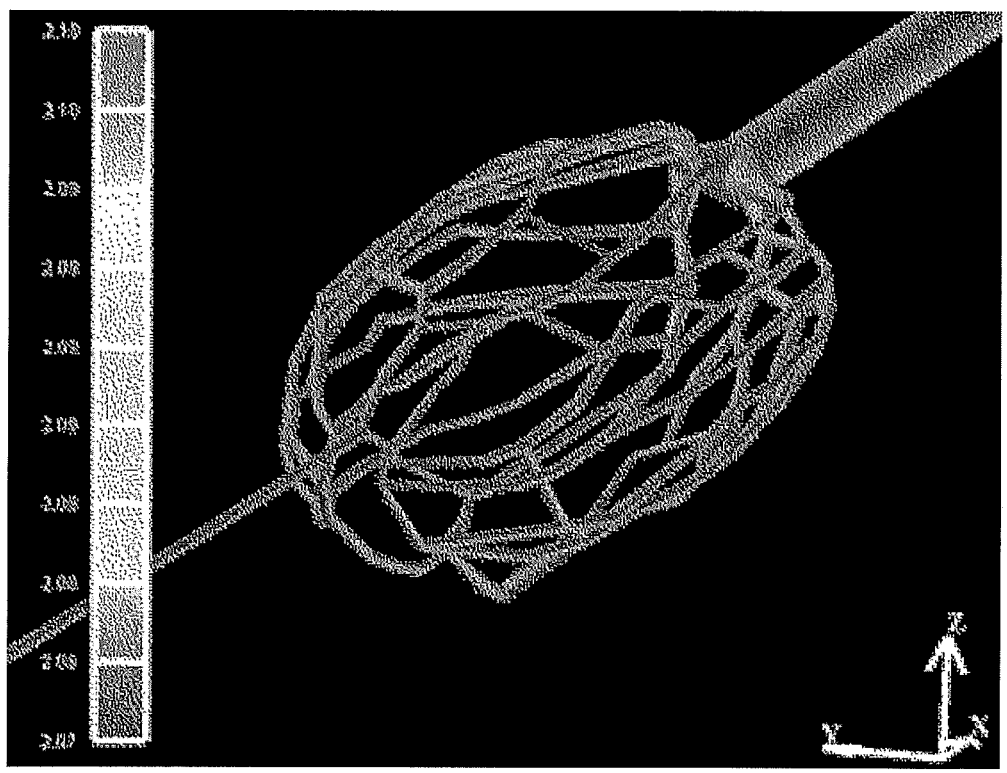
FIG. 17 illustrates a second exemplary display of a microcirculatory system.

FIG. 17 illustrates a second exemplary display of the microcirculatory system. In the example of FIG. 17 the microcirculatory system seen from an oblique direction is displayed.

Figure 18:
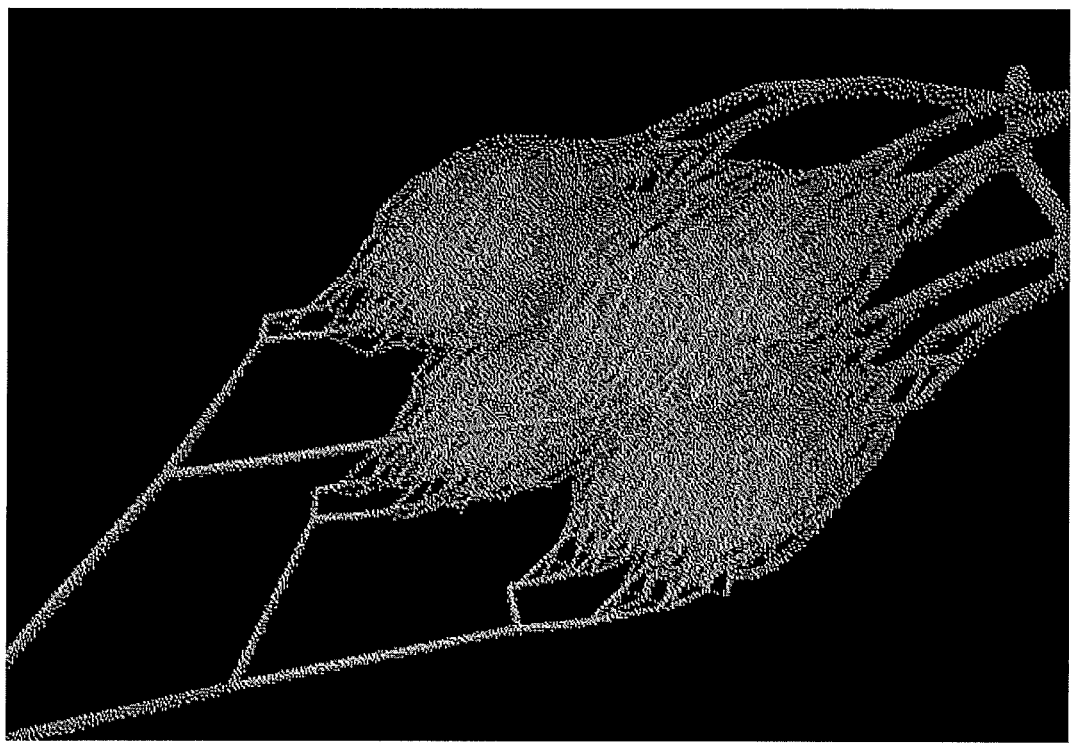
FIG. 18 illustrates a third exemplary display of a microcirculatory system.

FIG. 18 illustrates a third exemplary display of the microcirculatory system. In the example of FIG. 18, the symmetric region and the microcirculatory region are displayed simultaneously.

In FIGS. 16 to 18, difference between values of physical quantities is expressed by difference between colors, for example. The difference between colors is the difference between brightness and the difference between hues. For example, when displaying pressure, the color is set closer to red as the pressure value is higher, and the color is set closer to blue as the pressure value is lower. Also, when displaying oxygen concentration, the color is set closer to red as the oxygen concentration is higher, and the color is set closer to blue as the oxygen concentration is lower.

As described above, the microcirculation model formed on a two-dimensional plane is transformed into a three-dimensional structure to display simulation results, so that one can observe distribution of physical quantity and the like on a structure that is close to the actual vascular network. As a result, the state of a patient is easily understood, using simulation.

Although, in the second embodiment, the microcirculation model in the coronary circulation of the heart is transformed into a three-dimensional structure, the microcirculatory system of an organ other than the heart may be transformed into a three-dimensional structure in the same way.

According to one aspect, the simulation result of blood flow based on a two-dimensional circulation model is confirmed on a three-dimensional structure.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that various changes, substitutions, and alterations could be made hereto without departing from the spirit and scope of the invention.

What is claimed is:

1. A visualization apparatus comprising:
a memory configured to store a circulation model in which a vascular network, of an organ, having a diameter equal to or smaller than a predetermined value is defined on a two-dimensional plane, and a simulation result of a blood flow in the vascular network of the circulation model, the circulation model being a microcirculation model representing a structure of an arteriole, a venule, and a blood capillary between the arteriole and the venule by blood vessels; and
a processor coupled to the memory, the processor configured to perform a procedure including:
creating a cylinder having a length that is equal to a distance between both end points of the circulation model in the memory;
connecting terminals of first blood vessels of the arteriole and the venule to end portions of the cylinder;
locating second blood vessels of the blood capillary, represented in the circulation model in the memory, on the cylindrical surface, wherein the locating includes elongating the first and second blood vessels;
shrinking a length of each blood vessel of the first and second blood vessels to an original length, indicated in the circulation model, of the blood vessel;
shrinking the length of the cylinder, the length of the cylinder being shortened by a cumulative value of a cylinder-shortening length according to shrinkages of the first and second blood vessels, the cylinder-shortening length by each blood vessel of the first and second blood vessels being $\Delta vi (\cos \theta i)$, $\Delta vi$ being a blood vessel-shortening length of the blood vessel, $\theta i$ being an angle formed by a vector vi and a vector C, the vector vi being a vector from an end portion of the blood vessel to the other end portion of the blood vessel, the vector C being a vector passing through the cylinder center in a longitudinal direction of the cylinder; and
displaying the simulation result on a three-dimensional structure formed by the first and second blood vessels.

2. The visualization apparatus according to claim 1, wherein
the procedure further includes
creating the cylinder having a circumferential length of the cylindrical surface that is equal to a width of the circulation model in an orthogonal direction to a blood flow direction from an artery side to a vein side, and
locating a blood capillary on the cylinder.

3. A visualization method comprising:
creating, by a processor coupled to a memory configured to store a circulation model in which a vascular network, of an organ, having a diameter equal to or smaller than a predetermined value is defined on a two-dimensional plane, and a simulation result of a blood flow in the vascular network of the circulation model, a cylinder having a length that is equal to a distance between both end points of the circulation model in the memory, the circulation model being a microcirculation model representing a structure of an arteriole, a venule, and a blood capillary between the arteriole and the venule by blood vessels;
connecting, by the processor, terminals of first blood vessels of the arteriole and the venule represented in the circulation model in the memory to end portions of the cylinder;
locating, by the processor, second blood vessels of the blood capillary, represented in the circulation model in the memory, on a cylindrical surface, wherein the locating includes elongating the first and second blood vessels;
shrinking, by the processor, a length of each blood vessel of the first and second blood vessels to an original length, indicated in the circulation model, of the blood vessel
shrinking the length of the cylinder, the length of the cylinder being shortened by a cumulative value of a cylinder-shortening length according to shrinkages of the first and second blood vessels, the cylinder-shortening length by each blood vessel of the first and second blood vessels being $\Delta v_i (\cos \theta_i)$, $\Delta v_i$ being a blood vessel-shortening length of the blood vessel, $\theta_i$ being an angle formed by a vector $v_i$ and a vector $C$, the vector $v_i$ being a vector from an end portion of the blood vessel to the other end portion of the blood vessel, the vector $C$ being a vector passing through the cylinder center in a longitudinal direction of the cylinder; and
displaying a simulation result of a blood flow in the vascular network of the circulation model, on a three-dimensional structure formed by the first and second blood vessels.

4. A non-transitory computer-readable storage medium storing a computer program that causes a computer to perform a procedure, the procedure comprising:
creating, by a processor coupled to a memory configured to store a circulation model in which a vascular network, of an organ, having a diameter equal to or smaller than a predetermined value is defined on a two-dimensional plane, and a simulation result of a blood flow in the vascular network of the circulation model, a cylinder having a length that is equal to a distance between both end points of the circulation model in the memory, the circulation model being a microcirculation model representing a structure of an arteriole, a venule, and a blood capillary between the arteriole and the venule by blood vessels;
connecting, by the processor, terminals of first blood vessels of the arteriole and the venule represented in the circulation model in the memory to end portions of the cylinder;
locating, by the processor, second blood vessels of the blood capillary, represented in the circulation model in the memory, on the cylindrical surface, wherein the locating includes elongating the first and second blood vessels;
shrinking, by the processor, a length of each blood vessel of the first and second blood vessels to an original length, indicated in the circulation model, of the blood vessel
shrinking the length of the cylinder, the length of the cylinder being shortened by a cumulative value of a cylinder-shortening length according to shrinkages of the first and second blood vessels, the cylinder-shortening length by each blood vessel of the first and second blood vessels being $\Delta v_i (\cos \theta_i)$, $\Delta v_i$ being a blood vessel-shortening length of the blood vessel, $\theta_i$ being an angle formed by a vector $v_i$ and a vector $C$, the vector $v_i$ being a vector from an end portion of the blood vessel to the other end portion of the blood vessel, the vector $C$ being a vector passing through the cylinder center in a longitudinal direction of the cylinder; and
displaying a simulation result of a blood flow in the vascular network of the circulation model, on a three-dimensional structure formed by the first and second blood vessels.

* * * * *